US008229881B2

(12) United States Patent
Pedro et al.

(10) Patent No.: US 8,229,881 B2
(45) Date of Patent: Jul. 24, 2012

(54) SYSTEM AND METHOD FOR CREATING AND SEARCHING MEDICAL ONTOLOGIES

(75) Inventors: Vasco Calais Pedro, Pittsburgh, PA (US); Lucian Vlad Lita, San Jose, CA (US); Radu Stefan Niculescu, Malvern, PA (US); R. Bharat Rao, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 837 days.

(21) Appl. No.: 12/172,367

(22) Filed: Jul. 14, 2008

(65) Prior Publication Data

US 2009/0024615 A1 Jan. 22, 2009

Related U.S. Application Data

(60) Provisional application No. 60/950,064, filed on Jul. 16, 2007, provisional application No. 60/950,208, filed on Jul. 17, 2007, provisional application No. 60/952,020, filed on Jul. 26, 2007.

(51) Int. Cl.
*G06F 7/00* (2006.01)
*G06F 17/00* (2006.01)

(52) U.S. Cl. ...................................................... 707/600
(58) Field of Classification Search .................. 707/600, 707/789
See application file for complete search history.

(56) References Cited

U.S. PATENT DOCUMENTS

| | | | | |
|---|---|---|---|---|
| 7,512,273 B2 * | 3/2009 | Szummer | ..................... | 382/187 |
| 7,624,029 B1 * | 11/2009 | Ghouri | .............................. | 705/3 |
| 7,899,764 B2 * | 3/2011 | Martin et al. | ................... | 706/12 |
| 2005/0256949 A1 * | 11/2005 | Gruhl et al. | .................... | 709/223 |
| 2005/0286771 A1 * | 12/2005 | Bishop et al. | ................. | 382/202 |
| 2006/0271556 A1 * | 11/2006 | Mukherjee et al. | ............. | 707/10 |
| 2007/0094188 A1 * | 4/2007 | Pandya et al. | .................. | 706/45 |
| 2007/0203870 A1 * | 8/2007 | Saito | .............................. | 706/52 |
| 2008/0059391 A1 * | 3/2008 | Rosales et al. | ................. | 706/12 |
| 2008/0201280 A1 * | 8/2008 | Martin et al. | ................... | 706/12 |

OTHER PUBLICATIONS

Pedro et. al. "Okinet: Automatic Extraction of Medical Ontology from Wikipedia". AAAI. May 1, 2008.*
Pedro et. al. "Federated Ontology Search" SIIK 2006. Dec. 2006. Jogjakarta. Indonesia.*
Pedro, V. "Federated Ontology Search". Thesis Proposal. Language Technologies Institute School of Computer Science. Carnegie Mellon University. Oct. 5, 2006.*
Leroy et. al. "Meeting medical Terminology Needs—The Ontology-Enhanced Medical Concept Mapper". IEEE Transactions on Information Technology in BioMedicine. vol. 5 No. 4. Dec. 2001.*

* cited by examiner

*Primary Examiner* — Robert Beausoliel, Jr.
*Assistant Examiner* — Michael Pham
(74) *Attorney, Agent, or Firm* — Joshua B. Ryan (57) ABSTRACT

A method for creating and searching medical ontologies includes providing a semi-structured information source comprising a plurality of articles linked to each other, each article having one or more sections and each article is associated with a concept, creating a directed unlabeled graph representative of the information source, providing a plurality of labels, labeling a subset of edges, and assigning each unlabeled edge an equal probability of being assigned one of the labels. For each node, the probability of each outgoing edge is updated by smoothing each probability by an overall probability distribution of labels over all outgoing edges of each node, and the probability of each incoming edge is updated the same way. A label with a maximum probability is assigned to an edge if said maximum probability is greater than a predetermined threshold to create a labeled graph.

14 Claims, 9 Drawing Sheets

| Sample Feature Extraction | |
|---|---|
| Concept | fever |
| Document Title | Influenza |
| Header Path | Symtpoms and diagnosis > Symptoms |
| Context | Extreme coldness and fever |
| Link Type | regular |
| Part of List | yes |

For each node $C$, perform Steps 1 and 2, then repeat until convergence.

STEP 2.1. Let $p_{ik}$ be the probability of the $i^{th}$ outgoing edge (out of $n$ possible) from node $C$ to have the $k^{th}$ label (out of $m$ possible labels). Update the outgoing edge probabilities:

$$P_{ik} \leftarrow \frac{P_{ik} \times \sum_{j=1}^{n} P_{jk}}{\sum_{l=1}^{m} \left( P_{il} \times \sum_{j=1}^{n} P_{jl} \right)}$$

STEP 2.2. Update the incoming edge probabilities similar to the previous step.

STEP 2.3. Once convergence is reached via the above two steps, assign the maximum probability label to an edge as long as this probability is higher than a predefined threshold.

SYSTEM AND METHOD FOR CREATING AND SEARCHING MEDICAL ONTOLOGIES

CROSS REFERENCE TO RELATED UNITED STATES APPLICATIONS

This application claims priority from "Federated Medical Ontology System", U.S. Provisional Application No. 60/950,064 of Pedro, et al., filed Jul. 16, 2007, "Federated Medical Ontology System", U.S. Provisional Application No. 60/950,208 of Niculescu, et al., filed Jul. 17, 2007, and "Method for Automatic Creation of Ontologies From Semi-Structured Data Using Graph Algorithms" U.S. Provisional Application No. 60/952,020 of Pedro, et al., filed Jul. 26, 2007, the contents of all of which are herein incorporated by reference in their entireties.

TECHNICAL FIELD

This disclosure is directed to the automatic creation of medical ontologies from semi-structured data, and to retrieving and combining information from multiple ontologies in the medical domain.

DISCUSSION OF THE RELATED ART

In the last decades the number of available medical ontologies has grown considerably. Ontologies are an essential part of many approaches to medical text processing, understanding and reasoning. These ontologies enable the use of previous medical knowledge in a structured way. Applications of medical ontologies include: more effective search of patient records, hospital quality improvement programs, (semi)automatic ICD-9 coding for insurance reimbursement, preliminary symptom-based diagnosis, ambiguity reduction when choosing medical tests, and classification of diseases, symptoms, and other medical concepts. For example, when trying to answer whether a patient was prescribed Aspirin (for hospital quality improvement measures), one needs to consider similar terms (such as Ecotrin, Bayer pain reliever, etc). Also, when performing (semi)automatic patient ICD-9 coding, it is useful to map conditions that can be described in various ways (Heart Attack can be also stated as AMI or MI or Myocardial Infarction or simply Infarction). For preliminary diagnosis at the point of care, ontologies can help by quickly returning diseases that have a given set of symptoms, since instances of symptoms and diseases are concepts related by the "symptom of" relationship.

However, the creation of large, high quality medical ontologies is not trivial, requiring the analysis of domain sources, background knowledge, as well as obtaining consensus among experts. Several proprietary and public efforts such as MESH and SNOMED have become available. Even though it is considered a concrete domain, the quantity of concepts and the diversity of semantic types typically included in the medical domain increases its complexity to levels close to an open domain ontology. This suggests that the issues found in dealing with an open domain ontology are also present when dealing with the medical domain. Some evidence of this is given by the present number of ontologies, taxonomies, and dictionaries found within the medical domain. A comparison of available ontologies reveals both redundant and complementary coverage, but the variety of frameworks and languages used for ontology development makes it a challenge to merge query results from different ontologies. The number of available languages for ontological knowledge engineering such as RDF, OWL, DAML+OIL, and CYCL, combined with the existence of independent interfaces aggravates the issue. The lack of a formal way to access and combine the knowledge from different ontologies is an obstacle to more effective reuse and combination of these medical resources.

Current methods are labor intensive, prone to generate inconsistencies, and often require expert knowledge. Fortunately, semi structured information repositories, like Wikipedia, provide a valuable resource from which to mine structured information.

One approach to the multi-ontology issue is to absorb all the knowledge across sources into a common ontology typically casting it into a single format. The most relevant instance of this approach in the medical domain is UMLS, discussed below. However this approach has drawbacks, such as (1) non-scalability, (2) losing language and reasoning specificity of distinct ontologies, (3) losing privacy and autonomy of ontological knowledge, (4) language level mismatches such as syntax mismatches, differences in logical representation and different semantic primitives, and (5) ontology-level mismatches, such as difference in scope, coverage and granularity, making this challenge thus far too daunting in practice. Another approach is to bypass the merging issue and simply query more than one ontology via different interfaces, interpreting the results of each ontology individually, essentially moving the entire challenge from the ontology provider to the application builder. A third approach is to build an ontological middleware level for only small fragments of ontologies in an on-demand basis:

Query multiple ontologies and merge the query results from multiple knowledge base systems, much like federated search in information retrieval.

Follow ontological chains and inferences across ontologies, using partial query results from one ontology to query another. This is a more complex version of cross-database joins, where the data schemas are sufficiently compatible.

The main approaches to addressing these issues focus on ontology integration, by creating a mapping between the concepts and relations of different ontologies. In some cases, such as the Semantic Web project, the focus lies primarily on merging ontologies by establishing a full mapping among them.

Some efforts have tried to produce a merged ontology automatically using a bottom-up approach such as FCA-Merge; most involve some degree of semi-supervised mapping. Other approaches, such as the one taken by CYC, try to absorb other ontologies into a single main ontology while maintaining coherence. One disadvantage of these approaches is the prohibitive cost of producing a mapping or of absorbing an ontology, given their increasing scale and rate of availability. Another disadvantage is that it is not always possible to establish a one-to-one mapping between the concepts and relations in one ontology and the concepts and relations in another. Furthermore, there is the issue of keeping the mappings updated as the original ontologies evolve. A large number of available ontologies are considered works in progress and are updated frequently, which implies a constant updating of any mappings associated with those resources. Finally, the issue of the profitability of ontological creation is particularly important in the medical domain. Medical knowledge is generally produced by experts in the medical field, which are often very expensive resources. In order to maintain updated information in a particular medical field, it is necessary to create viable business models for ontological knowledge creation.

Most applications that use medical ontological information would benefit from an approach that models the information need, queries the relevant ontologies, and retrieves the best result while providing a single unified interface to the client application.

SUMMARY OF THE INVENTION

Exemplary embodiments of the invention as described herein generally include methods and systems for automatically creating medical ontologies from semi-structured data, such as Wikipedia, and to retrieving and combining information from multiple ontologies in the medical domain. According to an embodiment of the invention, a method for ontology creation uses an inclusive approach rather than a selective approach, where one starts by including all the article names as concepts and all the existing links as potential relations. One can subsequently rely on extracted features to assign labels, finally discarding links without labels.

According to an embodiment of the invention, a directed unlabeled graph is created that mimics the link structure, extracted features are used to generate a small amount of labeled data and a directional feedback edge labeling algorithm is used to extend the labels to the rest of the links, discarding the links with confidence below a preset threshold. The precision and recall of a method according to an embodiment of the invention were measured using a set of experiments that demonstrate the flexibility and utility of this approach. Given that our experiments were performed on a small dataset obtaining high performance, it is believed that a method according to an embodiment of the invention has the potential to achieve higher performance on larger datasets, further alleviating the amount of work required for ontology creation and further speeding up the process of knowledge acquisition.

A method according to an embodiment of the invention for retrieving and combining information from multiple ontologies uses a federated ontology search (FOS) in which one models ontologies as individual sources, constructs queries that describe the information need, executes them on each ontology independently, and finally merges the results into a single ranked list. Using a federated ontology search according to an embodiment of the invention one can parallelize query execution while respecting the structure of the individual ontologies, taking advantage of both redundant and complementary knowledge in the available ontologies to improve the overall performance of the system. A method according to an embodiment of the invention maintains ontology independence, allows for easier maintenance, enables the existence of viable ontology creation models and addresses the issue of dynamic ontologies, in which the continuous update to the ontology makes it costly to adopt a merge approach.

According to an aspect of the invention, there is provided a method for creating and searching medical ontologies, including providing a semi-structured information source comprising a plurality of articles linked to each other, each article having one or more sections, wherein each article is associated with a concept, creating a directed unlabeled graph representative of said information source, wherein each graph node is associated with a concept and each graph edge is associated with a link between concepts, providing a plurality of labels, and labeling a subset of said edges of said graph, assigning each unlabeled edge an equal probability of being assigned one of said plurality of labels, updating, for each node, the probability of each outgoing edge by smoothing each said probability by an overall probability distribution of labels over all outgoing edges of each node, updating, for each node, the probability of each incoming edge by smoothing each said probability by an overall probability distribution of labels over all incoming edges of each node, and assigning a label with a maximum probability to an edge if said maximum probability is greater than a predetermined threshold to create a labeled graph, wherein said labeled graph represents a new ontology adapted to being searched.

According to a further aspect of the invention, the method includes repeating said steps of updating, for each node, the probability of each outgoing edge and updating, for each node, the probability of each incoming edge.

According to a further aspect of the invention, the method includes discarding an edge if said maximum probability for a label is less than said predetermined threshold.

According to a further aspect of the invention, updating, for each node, the probability of each outgoing or incoming edge comprises calculating $$P_{ik} \leftarrow \frac{P_{ik} \times \sum_{j=1}^{n} P_{jk}}{\sum_{l=1}^{m} \left( P_{il} \times \sum_{j=1}^{n} P_{jl} \right)}$$

where $P_{ik}$ is the probability of edge i having label k, the sum in the numerator and the inner sum in the denominator are over all outgoing or incoming edges, and the outer sum in the denominator is over all labels.

According to a further aspect of the invention, labeling a subset of said edges of said graph comprises finding a first article having a list a concepts, finding an instance of a concept in said list of concepts in a section of a second article, and assigning a title of said section of said second article as a label of an edge from said second article to said concept.

According to a further aspect of the invention, labeling a subset of said edges of said graph comprises finding a concept in a list of concepts in a section of an article, and assigning a title of said section as a label of an edge from said article to said concept.

According to a further aspect of the invention, the method includes submitting a query to a plurality of ontologies, wherein each query comprises an operator expression, wherein each ontology returns one or more rooted directed acyclic graphs as a result of said query, wherein said graph nodes represents concepts and said graph edges represent links between concepts, calculating a similarity of each pair of graphs, and retaining those graphs whose similarity is greater than a predetermined threshold, for each pair of graphs $g_1$ and $g_2$ having a common subgraph, calculating tuple similarities for all pairs of tuples $t_1$ and $t_2$, where $t_1 \epsilon g_1$ and $t_2 \epsilon g_2$, for those tuples whose similarity is greater than a predetermined threshold, boosting a confidence of the tuples, and merging those graphs whose merger would yield a greatest confidence boost by adding edges not included in the common subgraph, to form $g_1 \cup g_2$.

According to a further aspect of the invention, the method includes, if a plurality of graphs remain after merging, scoring each graph based on the operator expression used in said query, and selecting a top scoring graph as representative of a best answer to said query.

According to a further aspect of the invention, each said operator is either a precision operator or a recall operator, wherein a score of a precision operator is calculated from $$S(r) = C_s \frac{\prod_i (c_{ei})}{\text{avg\_length}^k},$$

where $C_s$ is a confidence of an ontology S, $c_e$ is a confidence of an edge e, the product is calculated over all edges in a graph, avg_length is an average distance of paths contained in said graph, from root to leaf node, and k is a predetermined constant chosen to obtain a smooth curve, and a score of a recall operator is calculated from $$S(r) = C_s \times \left(1 - \frac{1}{\text{avg\_degree}^k}\right) \times \prod_i (c_{ei}).$$

where avg_degree is an average degree of the nodes contained in the graphs, and selecting a median score as final score for each result of an operator expression.

According to a further aspect of the invention, boosting said tuple confidence is calculated from $$1 - \prod_i (1 - C_i),$$

wherein $C_i$ is the confidence of edge I and the product is over all edges in a graph.

According to a further aspect of the invention, tuple similarity is calculated from $$sim(t_1, t_2) = \min \begin{cases} sim(c_{x1}, c_{x2}) \\ sim(c_{y1}, c_{y2}) \\ sim(r_1, r_2), \end{cases}$$

wherein a tuple $t_1 = (c_{x1}, c_{y1}, r_1)$, wherein $c_{xi}$, $c_{yj}$ are concepts and r is a link between concepts, and wherein a concept similarity $sim(c_{x1}, c_{x2})$ and a link similarity $sim(r_1, r_2)$ are each calculated using a Q-gram metric.

According to another aspect of the invention, there is provided a program storage device readable by a computer, tangibly embodying a program of instructions executable by the computer to perform the method steps for creating and searching medical ontologies.

DETAILED DESCRIPTION OF EXEMPLARY EMBODIMENTS

Exemplary embodiments of the invention as described herein generally include systems and methods for automatically creating medical ontologies from semi-structured data, and to retrieving and combining information from multiple ontologies in the medical domain. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The Wikipedia Structure

Wikipedia's general structure consists of an article name, which is unique within the particular wiki structure and thus suitable for a concept name, and links connecting articles, which are suggestive of semantic relations between them. Each article is typically divided in sections and sometimes contains tables that synthesize information pertinent to the article.

Within the different types of inter-article links, one can find redirects, which are articles that consist solely of a link to another article, and when this type of link is found one can interpret the two concepts described by those articles as synonyms. Each article is normally inserted into one or more categories, thus creating a set of hierarchical relations.

Even though each link seems to carry semantic information between two concepts, only a small percentage is typically used in mining Wikipedia, namely the redirects and categories. The main challenge of this work is to assign the correct semantic label to the extracted links deemed of interest, when the link is not a redirect.

Feature Extraction

For every link extracted a set of features is stored that are associated with that link. The set of features consists of the following:

Document Title The title of the document where the link was found. This corresponds to the source concept.

Section Header Path: The path composed of the sections up to the section where the link was found, e.g. Diagnosis→Symptoms.

Context: The context surrounding the link. This comprises the 3 words before and after the link.

Link Type: The type of link. This can be redirect, anchor, category or regular.

Figure 1:
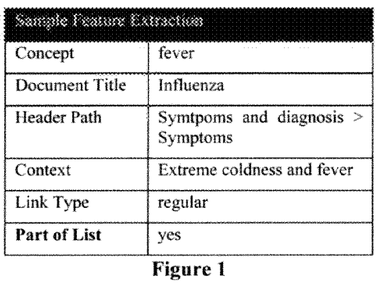
FIG. 1 is a table of sample features extracted from Wikipedia, according to an embodiment of the invention.

Part of List: Binary feature that is positive if the link was found within a list, such as Fatigue, Headache, Nausea, Vomiting. The table of FIG. 1 shows an example of the information that the extraction of one link generates. Even though the table shows five extracted features, this number of features is exemplary and non-limiting, and more or fewer features can be used in other embodiments of the invention.

Generating Labeled Data

Once the entire Wikipedia is processed, one has a directed unlabeled graph where each edge represents a relation between two concepts. For each edge there is also a set of associated features.

After selecting the set of labels of interest, one can use a combination of heuristics to bootstrap the labeling process. Besides using the redirect anchor and category links to label synonyms and hypernyms, the following two strategies are relied upon.

List Based Labeling: This strategy uses articles that list concepts and assigns labels to the instances of those lists that are under corresponding sections. For example, if fever is found under the section symptoms in article flu and fever is also in the list of medical symptoms article, then symptom is assigned as a label for the link between flu and fever.

Context Based Labeling: This strategy assigns the section title as label if the context shows that the link is displayed within a list. For example, if fever, headache and nausea are found under the section symptoms under article flu, one assigns symptom as a label for the link between flu and fever.

After the bootstrapping process, one has a directed graph with a partially labeled relation set. This graph forms the input for a graph probability propagation that labels the remaining links/relations in the ontology.

Directional Feedback Edge Labeling

A directional feedback edge labeling algorithm according to an embodiment of the invention starts with a small set of labeled links and uses graph probability propagation to label the remaining links/relations in the ontology. This algorithm relies on neighboring edge trends and directionality to update probabilities of possible labels that can be assigned to an unlabeled relation. The steps of this algorithm are described in FIG. 2.

Figure 2:
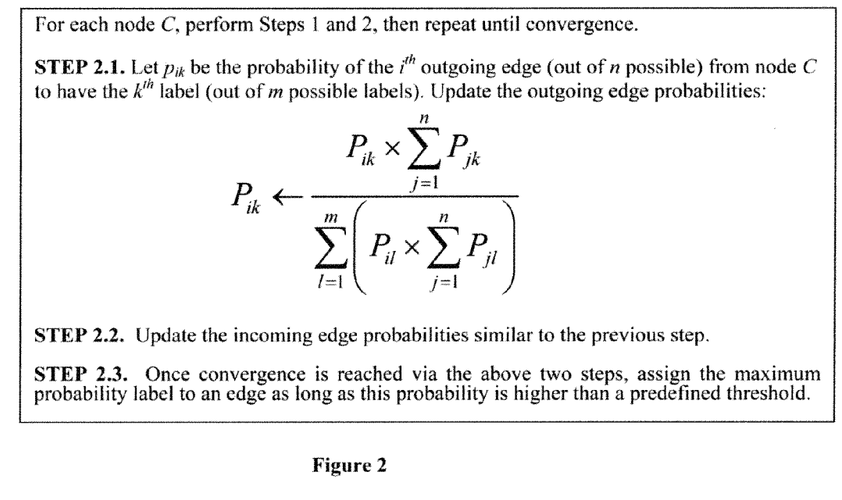
FIG. 2 presents pseudo-code for directional feedback edge labeling, according to an embodiment of the invention.
Figure 3:
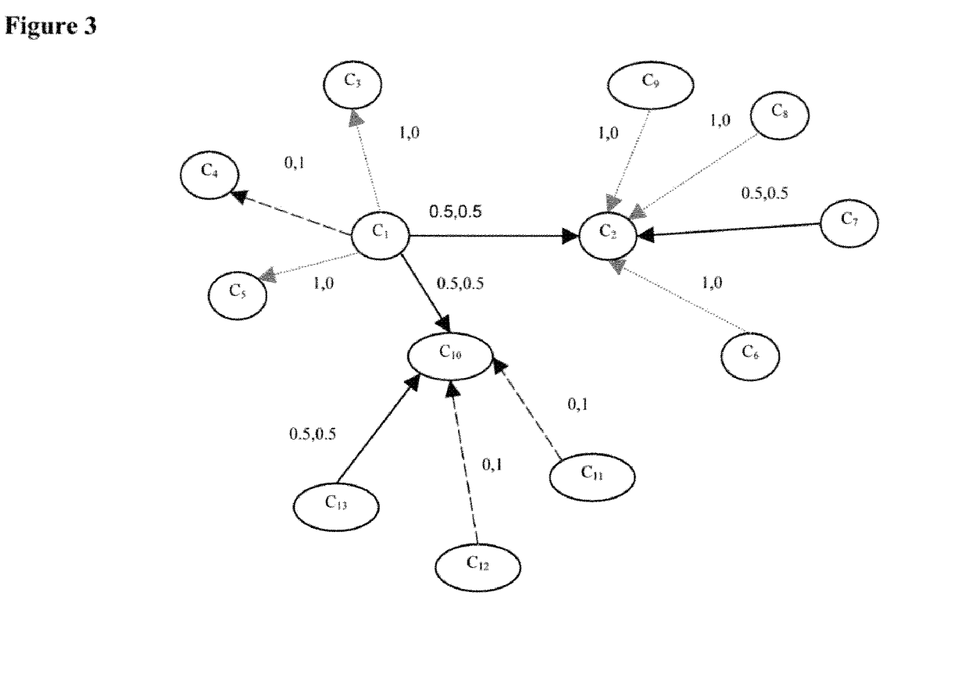
FIG. 3 is a graph depicting an example of directional labeling, according to an embodiment of the invention.

Referring now to the figure, each unlabeled edge starts with equal probability of label assignment. At each iteration, at step 1, for each node the probabilities of the labels of the outgoing edges are updated by smoothing them with the overall probability distribution of labels over the outgoing edges of that node, which is essentially multiplying the two probability distributions. This update is calculated from:

$$P_{ik} \leftarrow \frac{P_{ik} \times \sum_{j=1}^{n} P_{jk}}{\sum_{l=1}^{m} \left( P_{il} \times \sum_{j=1}^{n} P_{jl} \right)} \quad (1)$$

where $P_{ik}$ is the probability of edge i having label k, the sum in the numerator and the inner sum in the denominator are over all outgoing edges, and the outer sum in the denominator is m over all labels. This assures one takes into account both the current belief about that edge and the overall information contained in the edges going out of that node. To give an intuition why both types of information are important, consider FIG. 3, which depicts an example of directional labeling. The dashed and the dotted edges represent edges which were labeled during the bootstrapping phase. The dashed edges represent label SymptomOf and the dotted edges represent label Treats. The solid edges are unlabeled and therefore it is natural to assume that, in the absence of other information, each label is equally likely. However, based on the already labeled outgoing edges at $C_1$, the unlabeled edge $(C_1, C_{10})$ has a 2/3 probability to have label SymptomOf and 1/3 probability to have label Treats. Therefore, the initial belief of the edge $(C_1, C_{10})$ needs to be updated by incorporating this new information.

In step 2, the same calculation using EQ. (1) is performed for each node, but based on incoming edges. Because an edge is an incoming edge for a node and an outgoing edge for another, the label probability distribution for that edge is influenced by the label distributions at both its endpoints. Therefore, after a number of iterations, the label probabilities can be influenced by other label probabilities at any distance in the graph.

Referring back to the example in FIG. 3, the edge $(C_1, C_{10})$ has a 2/3 probability to be labeled SymptomOf if one looks only at the outgoing edges from $C_1$ whereas it has a probability of 1 to be labeled Treats if one look only at the incoming edges to $C_{10}$. This justifies the need to perform the same operation for both incoming and outgoing edges. The need to perform both steps iteratively is twofold: to assure convergence and to allow knowledge to propagate across the network.

After convergence, at step 3, only the edges with labels above a predefined threshold are selected, and the rest are discarded as unreliably labeled.

Ontological Search

Figure 4:
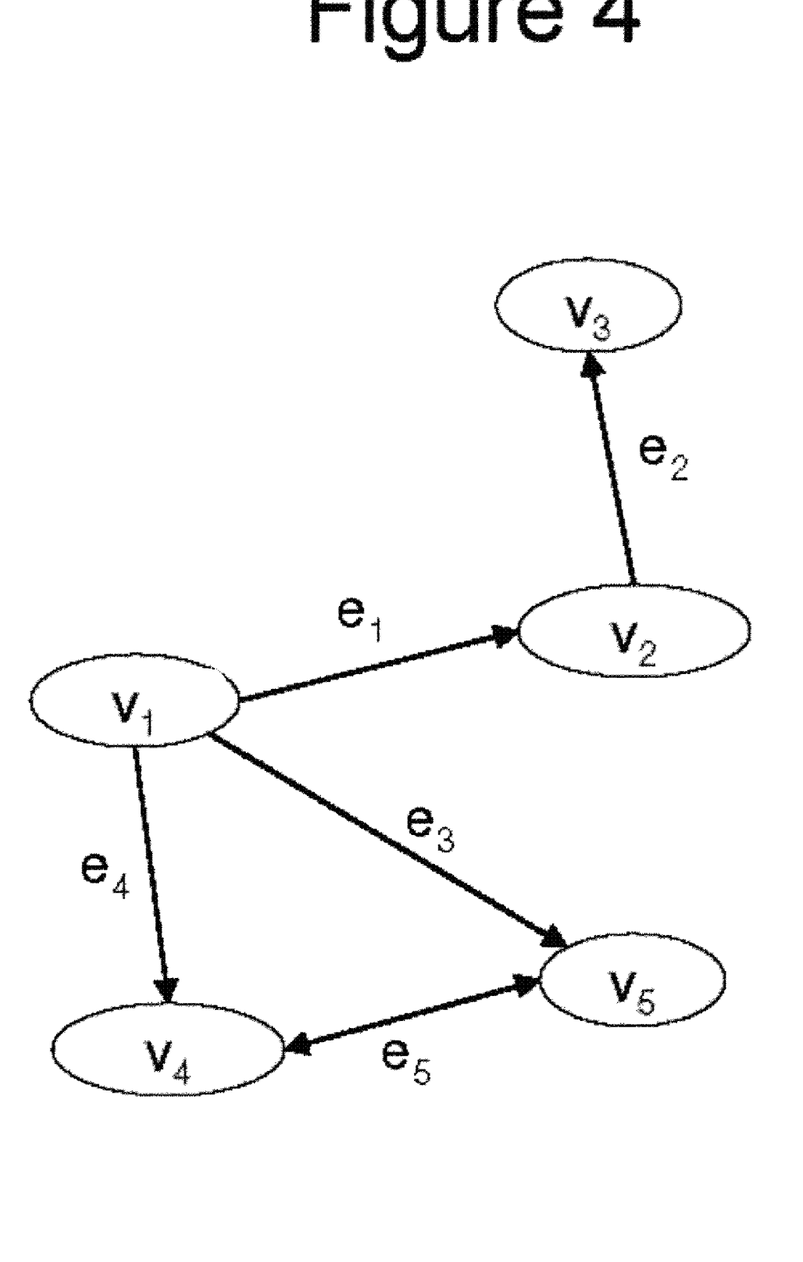
FIG. 4 shows an example of a rooted directed acyclic graph, according to an embodiment of the invention.

The success of an approach for retrieving and combining information from multiple ontologies according to an embodiment of the invention hinges on the definition of a search method that is independent of any particular ontology. For this purpose a concept of operator and a concept of query based on operators are introduced. The purpose of an operator is to decouple the search process from the information need. Instead of describing a complete semantic framework, the information request is described in terms of a decomposable query that can be transformed into a set of operators. This provides an elegant abstraction from the formal representations implemented by the ontological sources, allowing each operator to be an independent request. Note that defining a set of operators delegates responsibility for their execution to the ontologies themselves, therefore making no restrictions on whatever processes are executed in order to obtain the necessary information. This means that operators can be implemented using extended features of ontologies, such as inference, grounding, restrictions and theorem-provers, etc. The only constraint is that the output of each query execution is a Rooted Directed Acyclic Graph (RDAG). FIG. 4 shows an example of a RDAG, with nodes $V_1$, $V_2$, $V_3$, $V_4$, and $V_5$ representing concepts, and directed edges $e_1$, $e_2$, $e_3$, $e_4$, and $e_5$ representing links between concepts.

An exemplary, non-limiting set of operators according to an embodiment of the invention is as follows:

sim(C): Returns a graph of all concepts similar to concept C;

parents(C): Returns a graph containing the parents of C;
children(C): Returns a graph containing the children of C;
definition(C): Returns the definition of C;
conc($[C_1, \ldots, C_n]$, $[R_1, \ldots, R_n]$): Returns a graph of all concepts that are related to all concepts in C through relations in R;
rel($C_1$, $C_2$, $[R_1, \ldots, R_n]$): Returns a graph containing the path from $C_1$ to $C_2$ using relations in R;
syn(C): Returns the synonyms of C.

Figure 5:
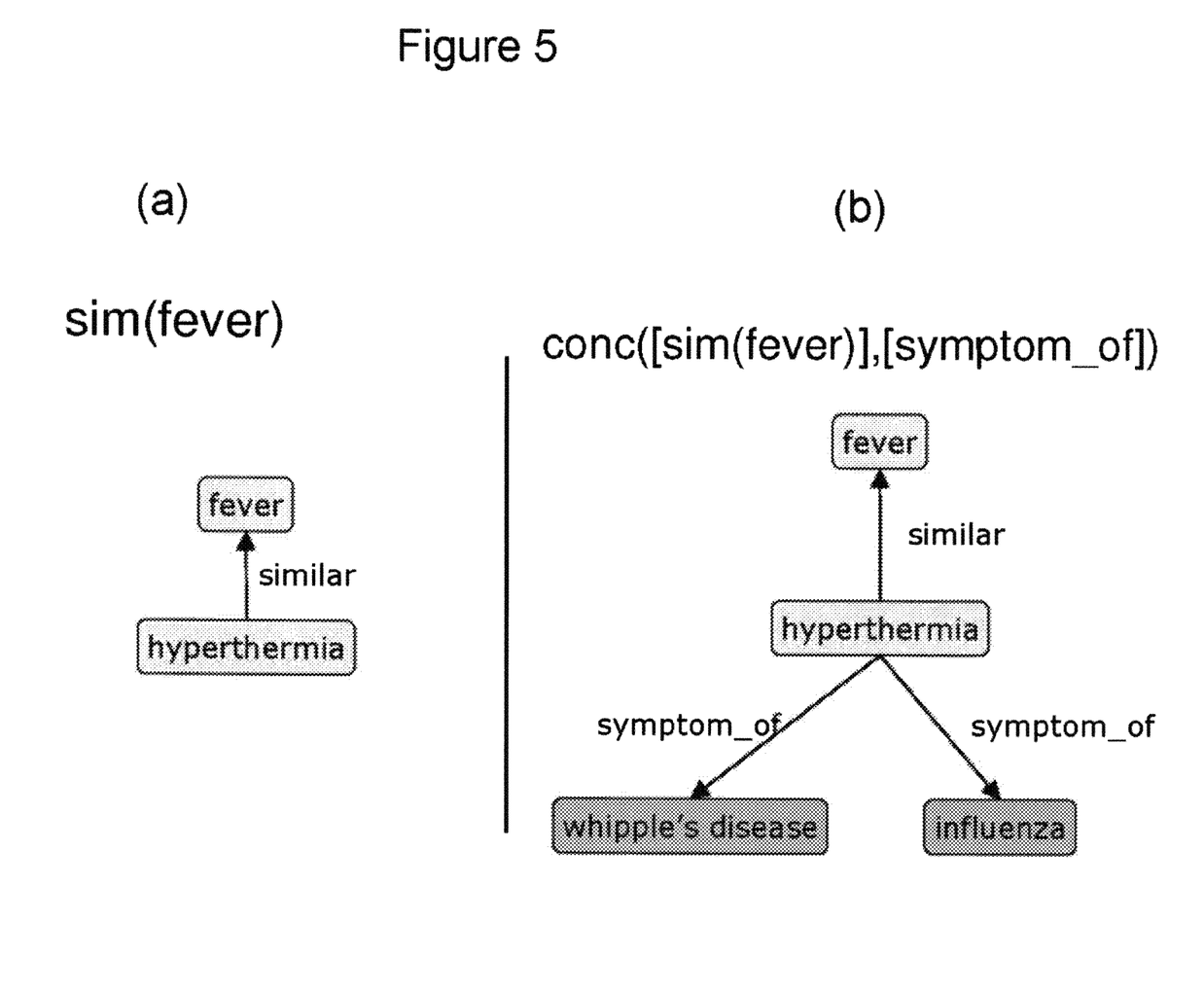
FIGS. 5(a)-(b) are graphs of exemplary operation results, according to an embodiment of the invention.

FIG. 5(a) is a graph of the result of the operation sim (fever), and FIG. 5(b) is a graph of the result of the operation conc([sim(fever)], [symptom_of]). All operators have the property of compositionality to enable the construction of complex operations based on simpler ones. The ideal operator set should contain the operations usually performed in ontologies.

There are three aspects of federated searching that are relevant: resource description, resource selection and results merging and scoring. In the ontological domain, resources are ontologies.

Ontology Description and Selection

It is desired to select a subset of the available ontologies based on some measure of appropriateness of an ontology given a query. This can be modeled as the probability p(O, q), where O is an ontology and q is a query.

Distributed online efforts typically result in ontologies that are constantly updated thus making the task of modeling them challenging. One should also consider cases where the ontologies make use of inference engines and logic mechanisms.

Therefore, an approach according to an embodiment of the invention is to evaluate the relative utility of different ontologies by comparing the results they produce for a given input query. Although theoretically one could create a gold set of queries to perform on each ontology and use the results to create an ontology model, due to the diverse nature of ontologies, this is in practice a challenging task. One could use a naive approach where the query is executed in the subset of ontologies that contain the concepts in the query, but this has issues in both performance and accuracy. To mitigate this risk, according to an embodiment of the invention, a parameter that models the general accuracy for a given source was created. This parameter can be tuned/learned in several ways. For example, it can be based on an expert evaluation of the source. For the medical domain, on a 0 to 1 scale, Wikipedia's score is 0.5, UMLS's score is 0.9, and Wordnet's score is 0.4 as it pertains to relevance and level of noise in the results returned by searching in each source. The weight given to some sources, such as Wikipedia, can be increased over time, if Wikipedia tends to provide the most useful results. In addition, a parameter model can adjust for trustworthiness by adjusting the result ranking for future queries. Further, different parameters can be adjusted separately for trust, noise, volume of relevant answers, etc. An accuracy parameter according to an embodiment of the invention is a good candidate for the application of a learning algorithm such as a variation of the Expectation-Maximization algorithm. However, gold standards are needed to train and test such algorithms, which makes the process time consuming.

Merging

One feature of an approach according to an embodiment of the invention is that rather than trying to merge two entire ontologies, only the results are merged. This reduces the task of merging ambiguous concepts given that queries are grounded in a query concept and therefore only relations that apply to the concept in the query are returned. Polysemic concepts will be explicitly modeled via separate results, with a variable confidence on the relations contained in each result.

The structured nature of the query results implies that the result merging task in the ontology domain is different from result merging in a federated text search, where the results typically consist of unstructured data. In the case of an ontology search the results are graphs, which allows treating merging as an instance of inexact graph merging. While one of the goals of merging in federated searching is to eliminate duplicates, a goal of merging in ontology searching is to find complementary information and to produce, at the top-ranked position, the most complete and accurate result. Generally speaking, one wants to merge two results if they represent information about the same concepts, thus creating a more complete result.

As an example, consider three distinct ontologies, $O_1$, $O_2$ and $O_3$. Assume that one can execute the query sim(bank), to find concepts similar to bank. Imagine that ontology $O_1$ and $O_2$ both interpret bank as river bank while ontology $O_3$ interprets bank as money bank. Given this scenario, one would like the result set to contain two results, one referring to the concepts similar to river bank and the other to the concepts similar to money bank. The results from O1 and O2 should be merged since that is likely to yield an increase in the quantity of information contained in the result, as well as the confidence in the concepts common to the two results.

The task can be formulated as follows. Given two RDAGs $g_1$ and $g_2$ it is desired to merge the two graphs if they are similar. Typically this is done by considering one of two options, either measuring the similarity between the graphs or measuring the difference. But in this case one not only wants to measure the similarity but also find the maximum common subgraph. One can look to the science of inexact graph matching for guidance here.

Inexact graph matching occurs when one does not expect to find an isomorphism between the two graphs to be merged. This is one of the most complex tasks in computer vision and is also an important part of chemical similarity searching. More specifically, inexact graph matching has been proven to be an NP-Complete problem.

Graph Similarity

Graph similarity distance is typically calculated in one of the following ways: cost based distance, feature based distance, or maximum common subgraph.

Cost based distance is based on edit operations on the graph, and typically adds nodes or edges, removes nodes or edges, or re-labels nodes or edges, where each operation is associated with a cost. Given two graphs $g_1$ and $g_2$, the edit distance between $g_1$ and $g_2$ is the minimum number of edit operations necessary to transform $g_1$ into $g_2$.

Feature based distances use a set of invariants established from the graph structural description, using these features in a vector representation to which distance or similarity measures are applied.

The maximum common subgraph technique finds the largest subgraph common to both $g_1$ and $g_2$. To address this requirement, current approaches use the concept of maximum clique detection. The task is then changed into finding the maximum common edge subgraph. According to an embodiment of the invention, a variation of the overlapping coefficient for graphs is used, a measure whereby if graph g contains $g_0$ or the converse then the similarity coefficient is a full match.

Localized Confidence Boosting Algorithm

Given $g_1$ and $g_2$ as results of a query, an algorithm according to an embodiment of the invention is as follows. A screening procedure is applied to calculate an upper bound of the maximum common subgraph so that as much of the graphs can be discarded as possible. An exemplary, non-limiting screening procedure is based on the Rascal algorithm, which calculates graph similarity using maximum common edge subgraphs. After applying the screening procedure, one is left with graphs where similarity between $g_1$ and $g_2$ is above a certain threshold T: sim(g1, g2)>T. This threshold can be tuned by any number of methods as are known in the art. The result is basically $g_1 \cap g_2$ which is the maximum common subgraph being sought. However, this does not take into consideration certain situations for calculating the subgraphs, such as different granularity. One can now apply localized boosting and then add the nodes and edges that were previously discarded.

The basic intuition behind the confidence boosting is that the confidence of the edges is boosted whenever two edges are merged. The boosting is determined through the use of the SoftOr, given by the formula:

$$1 - \prod_i (1 - C_i), \tag{2}$$

where $C_i$ is the confidence of edge i. The edge confidence is usually, but not always, encoded in the ontologies, and represents how confident the ontology is on that particular assertion. For those ontologies that do not provide such confidence, a default value is manually assigned, such as 0.8 for Wordnet.

To apply confidence boosting one can apply the concept of tuples, where $t_x = (c_x, c_y, r)$ is a tuple, $c_x, c_y$ are concepts and r is a relation. Note that concepts correspond to graph nodes and relations to graph edges. First split $g_1$ and $g2$ into tuples $t_x = (c_x, c_y, r)$, where $c_x, c_y, r \in g$, such that $c_x$ and $c_y$ are adjacent and $r(c_x, c_y)$. The sets of tuples from $g_1$ and $g_2$ are compared and if sim($t_x, t_y$)>T then the confidence of $t_x$ is boosted by the amount specified by the SoftOr formula of EQ. (2), above.

Tuple Similarity

Tuple similarity measures are based on linear combinations of the edge similarity and the concept similarity. When comparing concepts or relations, one use the Q-Gram distance on the strings that represent them. The intuition behind the use of q-grams as a distance metric is that when two strings $s_1$ and $s_2$ are within a small edit distance of each other, they share a large number of q-grams in common. In particular, the q-gram distance is a (pseudo) metric for measuring the distance between two strings. It can be used to determine if two strings matches each other with less than k errors. The q-gram distance is calculated by counting all occurrences of all substrings of length q in two strings and finding the difference in the occurrence count between the strings. This metric is fairly robust to orthographic errors, morphological errors and compound words, which makes it suitable for use with an embodiment of the invention. The similarity between two tuples is given by the minimum similarity of the concepts and relations contained in the tuples. Formally:

$$sim(t_x, t_y) = \min \begin{cases} sim(c_{x1}, c_{x2}) \\ sim(c_{y1}, c_{y2}) \\ sim(r_x, r_y), \end{cases} \quad (3)$$

Scoring

Even after merging graphs with common subgraphs, one might be left with multiple graph results from the query. In this case, one then computes a score for each graph based on the operators used for the query. The final result would be the graph with the highest score. A result is scored in a compositional manner, by scoring the outcome of each operator used in a query individually before calculating the final score. A ranking will be computed from the scores of the results. According to an embodiment of the invention, the final score is calculated from the median operator score.

Each operator focuses on either recall or precision. Operators that focus on recall will typically return results with as much information as possible. The similarity operator, for example, returns all the synonyms associated with a concept, and the more synonyms the better the result should be, all else being equal. Operators that focus on precision will usually return chains of associations. They focus on precision of the relations. As an example, the relation operator finds the relation between two concepts All else being equal, a direct relation would be better than a long chain of relations.

When a result is merged from two other results, the confidence in the sources from where the results were extracted is combined using the SoftOr rule of EQ. (2), as described before. Two scoring metrics are now presented, to be used by precision type operators and recall type operators respectively.

Precision scoring metric: This scoring metric gives preference to shorter graph lengths. Given that this metric is used for precision type operators, it is desirable to have results with short chains.

$$S(r) = C_s \frac{\prod_i (c_{ei})}{\text{avg\_length}^k}, \quad (4)$$

where $C_s$ is the confidence of the source, $c_e$ is the confidence on the edge and avg_length is the average distance of the paths contained in the graph, from root to leaf node. The constant k is determined heuristically in order to obtain a smooth curve. According to an embodiment of the invention, an exemplary, non-limiting value is k=4.

Recall scoring metric: The recall scoring metric gives preference to graphs with large node degrees. Given that this metric is used by recall type operators, the score should increase with the quantity of diverse information contained in the graph. Thus $$S(r) = C_s \times \left(1 - \frac{1}{\text{avg\_degree}^k}\right) \times \prod_i (c_{ei}), \quad (5)$$

where avg_degree is the average degree of the nodes contained in the result.

Figure 6:
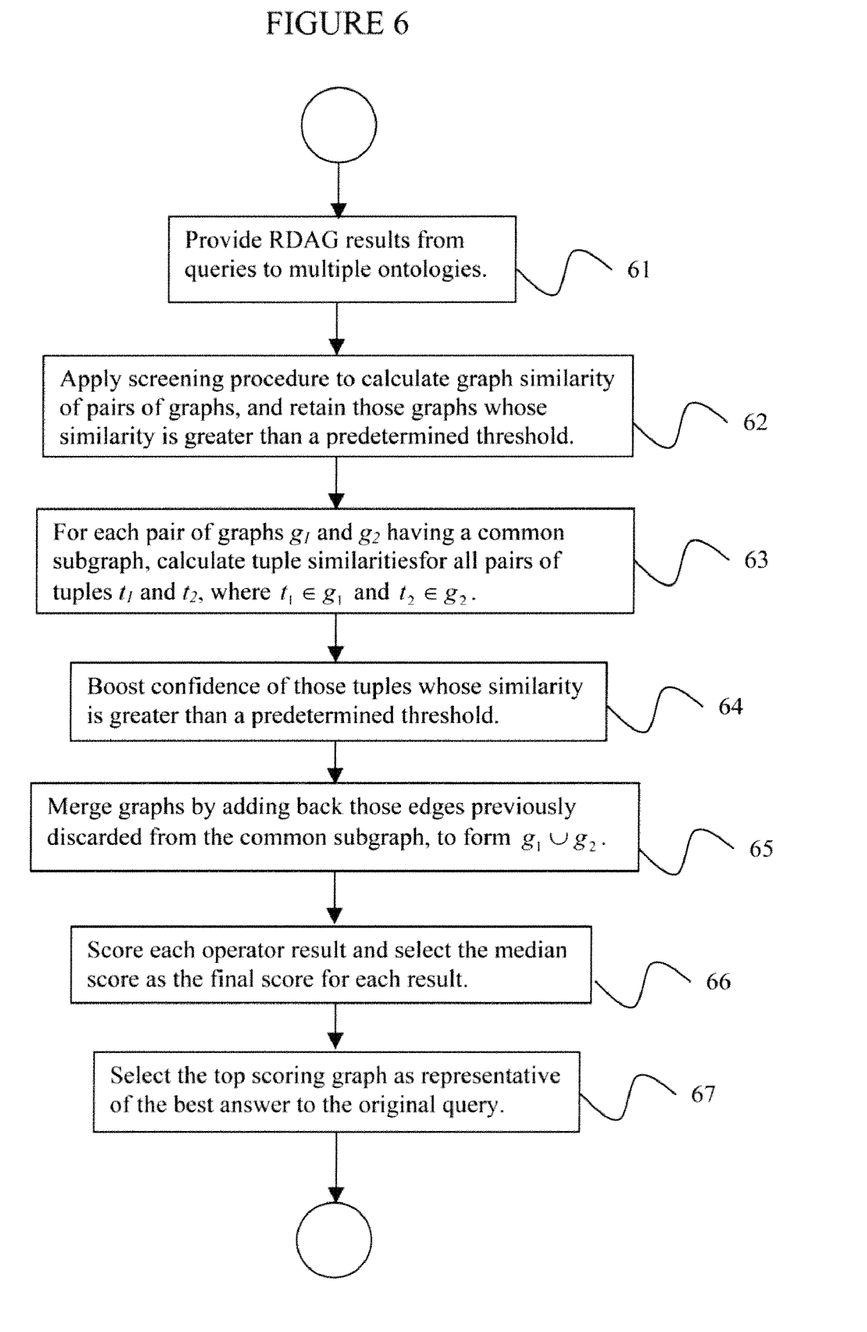
FIG. 6 is a flowchart of a method of merging and scoring query results, according to an embodiment of the invention.

A flowchart of a method of merging and scoring query results is presented in FIG. 6. This method assumes that a query implemented as an operator expression has been submitted to a plurality of ontologies, and that the results have been received. Each result is a RDAG as described above, with possibly more than one result being returned from each ontology. These resultant RDAGs are provided at step 61. To determine which graphs to merge, one next measures the similarity of the graphs, to see if there is any overlap. At step 62, a screening procedure is applied to calculate graph similarity of pairs of graphs, and those graphs whose similarity is greater than a predetermined threshold are retained. Typically, these graphs will have a common subgraph, as described above. At step 63, for each pair of graphs $g_1$ and $g_2$ having a common subgraph, tuple similarities are calculated from EQ. (3) for all pairs of tuples $t_1$ and $t_2$, where $t_1 \in g_1$ and $t_2 \in g_2$. For those tuples whose similarity is greater than a predetermined threshold, the confidence of the tuples is boosted at step 64 according to the SoftOr rule of EQ. (2). Those tuples whose merging would yield the greatest confidence boost are merged. The merging is completed at step 65 by adding back those edges previously discarded from the common subgraph, to form $g_1 \cup g_2$. Since there may still be multiple graphs after merging, the remaining graphs are scored based on the operator expressions used to yield the graph result. Each operator result is scored at step 66 using either EQ. (4) or EQ. (5), and, according to an embodiment of the invention, the median score is selected as the final score for each result. Finally, at step 67, the top scoring graph is selected as representative of the best answer to the original query.

Figure 7:
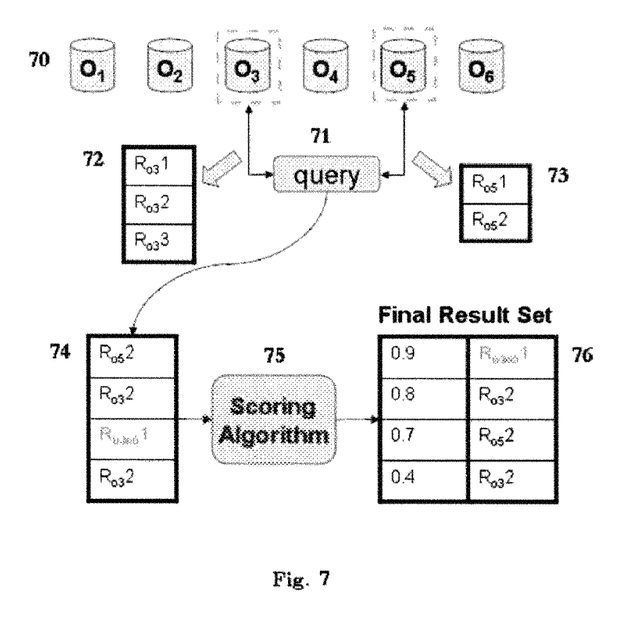
FIG. 7 depicts a query example according to an embodiment of the invention.

A schematic diagram of a query is shown in FIG. 7. Referring now to the figure, a plurality of ontologies $O_1, \ldots, O_6$ are shown. A query 71 is submitted to ontologies $O_3$ and $O_5$, yielding results $R_{O_3}1$, $R_{O_3}2$, $R_{O_3}3$ from $O_3$, and $R_{O_5}1$ and $R_{O_5}2$ from $O_5$. The graph similarity analysis results in results $R_{O_3}1$ and $R_{O_5}1$ into $R_{O_3O_5}1$, shown with the merged results 74. The scoring algorithm 75 then yields a final result set 76 showing scores of each query result.

Characterization of Medical Resources

The available medical ontological resources can be divided according to several characterizing dimensions: scope, depth, cost and noise.

Scope is the coverage as defined by the percentage of broad semantic topics covered by the ontology. Ontologies can vary according to coverage. The broader the coverage the more diverse is the ontology.

Ontology depth is defined by the average path length in the ontology, or equivalently, the average number of concepts in each semantic type. The longer the average path, the more specialized is the ontology.

Cost is defined by $T_c \times C_c$, where $T_c$ is the amount of time in human hours required per concept and $C_c$ is the cost in dollars per concept. The range varies from fully automatic ontologies, which require almost no human effort, to specialized, fully manually generated ontologies, which not only require a large amount of time per concept but also a highly specialized (and therefore expensive) human to generate that knowledge.

Noise is defined by the percentage of concepts in the ontology that carry no semantic meaning. Given a set of concepts, a human should be able to determine which concepts carry semantic meaning. This is relevant in automatically created ontologies that tend to introduce semantically irrelevant concepts due to the extraction process.

Figure 8:
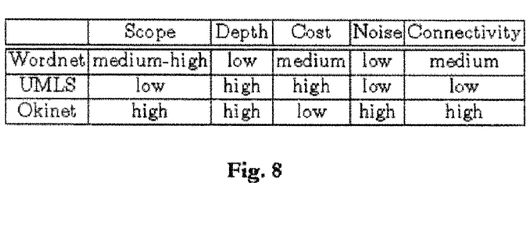
FIG. 8 is a table that characterizes three ontologies, according to an embodiment of the invention.

Any ontology can be categorized according to these four measures. Typically there is an inversely proportional relation between coverage and depth. Characterizations of three ontologies according to an embodiment of the invention are presented in the table of FIG. 8. The scale presented in this table is meant to describe ontologies in a broad sense only. Generally speaking, it should be possible to compare any two ontologies given these dimensions. Note that there are possibly many other characterization schemes for ontologies, although they may contradict the characterization of FIG. 8. Next are described some examples of different ontology types according to the characterization given above.

Wordnet

WordNet is a semantic lexicon for the English language. It is perhaps the most widely used ontology in the world. It groups English words into sets of synonyms called synsets, provides short definitions, and records the various semantic relations between these synonym sets. It currently holds 155327 unique strings. It the canonical example of an ontology with high coverage, low depth and medium cost.

Unified Medical Language System

The National Library of Medicine's Unified Medical Language System (UMLS) is both an ontology and a set of ontologies. It aims to bring together a set of medical dictionaries (currently holding roughly 100) and contains information about medical concepts, semantic types, and the relations between concepts and semantic types. It maintained mostly by hand and it is the result of a 15 year long project that involved many thousand of man hours, including developing and making concrete affirmations backed by paper citation. It currently contains over 1 million concepts. UMLS represents the current largest effort of manual ontology mapping. Due to the structure of UMLS, certain semantic relations exist only at the semantic network level. This means that in UMLS one cannot determine symptoms of particular diseases, but rather between classes of concepts. For example, one cannot determine the symptoms_of flu, but rather what categories of concepts could represent symptoms of flu. Due to its specific nature and medical domain expertise, UMLS has low coverage (it deals mostly with the medical domain), high depth (it is very specialized) and has a high cost (the nature of the knowledge it contains requires very specialized knowledge providers).

Okinet

Okinet is a Wikipedia based Ontology being currently developed at Siemens Research based on ontologies creation methods according to an embodiment of the invention as described above. Okinet presents a unique set of challenges in the sense that it is an ontology derived from a source that is updated very frequently. Any method other than a fully autonomous will have challenges in updating the ontology. At the same time, it highlights the challenges of maintaining mappings between ontologies, given that not only the number of concepts included in Wikipedia is enormous, but also that the update frequency is high. Therefore it aims to bring together a set of machine learning and natural language techniques to automatically create an ontology from Wikipedia, without human supervision. In addition to information previously extracted, a combination of feature based and graph based approaches are used to build the ontology. Okinet currently contains more than 4 million concepts and encodes a wide range of semantic relations from more traditional relations such as synonyms, hypernyms, etc., as well as instance based semantic relations such as symptom_of, causes, medication, etc. It represents the opposite approach to UMLS, being the automatic creation of an ontology from a semi structured document corpus. Okinet is high coverage (it is an open domain ontology), high depth (it is incredibly rich) and low cost (the knowledge exists already) ontology. One could argue that the cost of creating Wikipedia should be considered when considering the cost of creating Okinet, but given that the knowledge was not created specifically for Okinet, it is not part of these calculations. Okinet thus exist as complement to UMLS, allowing the rapid and automatic creation of relations at the instance level, which enables the use of inference processes using both ontologies.

UMLS Issues

Even though UMLS an extremely rich and large ontology, it presents some challenges regarding certain types of relation types. UMLS provides two different knowledge sources, the Metathesaurus and the Semantic Network. The Metathesaurus establishes relations at the concept level and the Semantic Network describes the relations at the semantic type level. The challenge is due to the fact that there is no direct correlation between the two in most cases. Even though some work has been done in mapping the two relation sets, it is currently not possible to retrieve information regarding semantic relations between concepts that belong to specific semantic types other than hierarchical information, e.g., "What is the medications that treat disease X?" is a question that is not possible to answer using UMLS. An embodiment of the invention can leverage the use of multiple ontologies to fill the gaps in UMLS, thus creating a very powerful ontological solution.

Experimental Setting

In order to test a method according to an embodiment of the invention for automatically creating a medical ontology, Wikipedia was used as a test case, even though the methodology could be applied to any other wiki-like resource. It is desired to create an ontology of causes, treatments, symptoms, diagnoses and side effects.

A method started by selecting all the concepts contained in the list of diseases article, which contains 4000+ diseases and syndromes, then expanding the article set to include all the articles that linked or were linked to by any of the articles contained in the current set.

Figure 9:
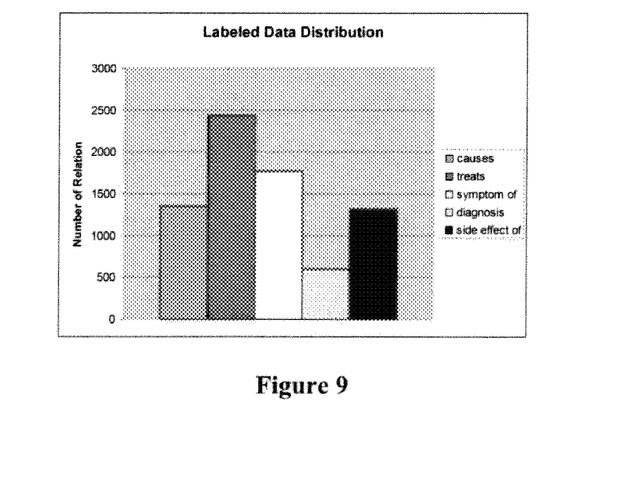
FIG. 9 is a table that shows the distribution of relation labels for an ontology, according to an embodiment of the invention.

Next, the feature extraction process was performed followed by the bootstrapping procedure. The results were manually checked to create a gold standard set. This resulted in an ontology with 4308 concepts and 7465 relations divided. FIG. 9 is a table that shows the distribution of relation labels for this ontology.

Experiments were performed using a small percentage of the labeled data as a training seed for a directional edge feedback labeling algorithm according to an embodiment of the invention while considering the remaining edges unlabeled. The results of the labeling algorithm were then compared with the original labels. In these experiments, both the percentage of the labeled training data (seed size) as well as the threshold above which a label was assigned were varied. The results were evaluated using precision and recall. Precision is the percentage of label assignments that were correctly assigned to the proper class, while recall is the percentage of possible labels that were correctly assigned.

Figure 10:
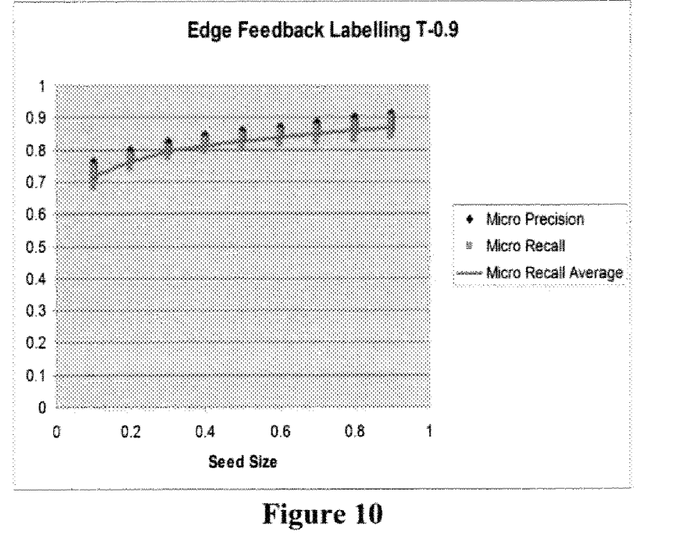
FIG. 10 is a graph of the precision and recall results as a function of varying the size of the labeled seed set, according to an embodiment of the invention.

FIG. 10 is a graph of the precision and recall results as a function of varying the size of the labeled seed set at a threshold for label assignment of 0.9, which means that only labels with a high confidence are assigned. The seed size is shown as a percentage of the total set size. Even though only micro precision and micro recall are shown in the figure, the results for macro precision and recall were very similar and were thus not presented for purposes of clarity. Each point in the average line represents 100 runs with a labeled seed size of the indicated value. The precision and recall average vary between 70% and 90% while seeds vary from 10% to 90% of the total labeled set.

Figure 11:
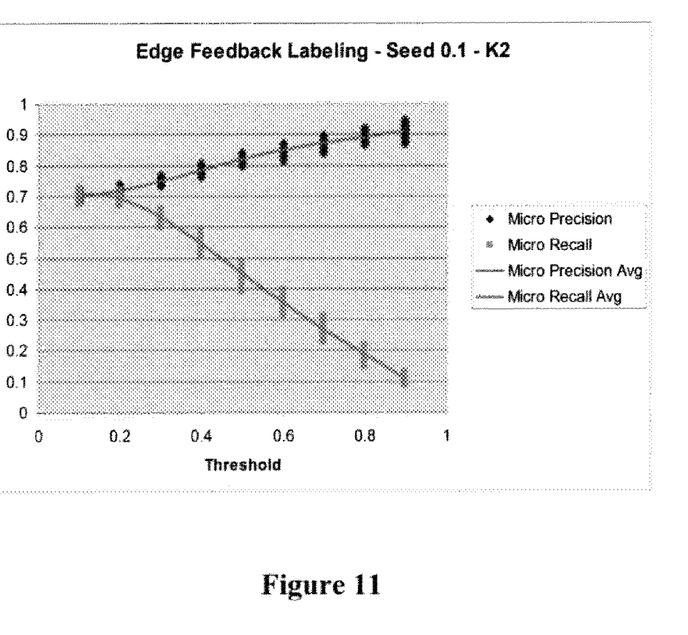
FIG. 11 is a graph showing the precision and recall results of stopping the labeling algorithm after two iterations, according to an embodiment of the invention.

Even though the results are very promising, other ways to boost the results at small seed sizes were explored. Due to the propagating nature of this algorithm, by stopping after a few iterations, one is in fact preventing long-range labeled edge influences and therefore one can restrict the process of labeling an edge to local neighborhood in the graph. FIG. 11 shows the precision and recall results of stopping the labeling algorithm after two iterations, using a 10% seed size and varying the assignment threshold. Given the number of iterations, only edges with a fast convergence rate will update the probabilities distribution enough to get assigned a label. This means that the higher the threshold, the more accuracy is obtained, even though the recall is sharply reduced. This variation is useful in situations where the precision is more important than recall. Using this technique one could extend the labeled data set with highly accurate labels.

Figure 12:
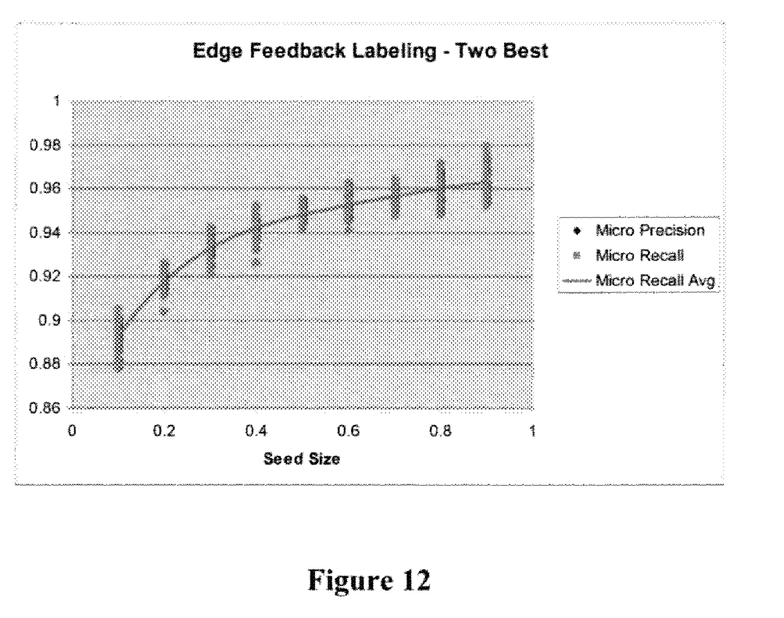
FIG. 12 is a graph showing the precision ands recall results of taking the two highest confidence labels for each edge, according to an embodiment of the invention.

Finally an algorithm according to an embodiment of the invention was considered as way to reduce uncertainty. FIG. 12 shows the precision ands recall results of taking the two highest confidence labels for each edge and considering each as correct if either of the assigned labels is correct.

Ontology Search System

The inventors have currently have integrated UMLS, Okinet and Wordnet as a proof of concept application. An ontology search system according to an embodiment of the invention was built that uses a federated approach to ontology search as described above and a simple interface for ontology search was produced. This system allows for rapid access to the ontological knowledge in the ontologies contained therein. In particular, the target domain is the medical domain, where there are multiple ontologies, lexicons, and general graph-based resources covering specific parts of the medical knowledge space. In this scenario, a federated ontology search engine is useful. An ontology search system according to an embodiment of the invention supports multiple ontologies running in parallel.

Web Based Interface

Although a search system according to an embodiment of the invention works in a typical server fashion, which can be queried directly using XML, a visualization tool for ontology browsing was also created. Given the fact that the server is querying several ontologies, possibly using resources that span several servers, having a localized copy of everything is unfeasible. Thus, a web interface was created to visualize the results of ontology queries. The web interface allows for querying an ontology search system according to an embodiment of the invention for synonyms and medical relations from all the available ontologies. It enables a user to visualize the desired relations across ontologies in a graph display and to browse subsequent relations with ease and simplicity. Results from different ontologies, such as Wordnet, UMLS and Okinet, can be represented by different colors. According to an embodiment of the invention, it uses AJAX and JSP with JSON as a communication protocol.

System Implementations

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 13:
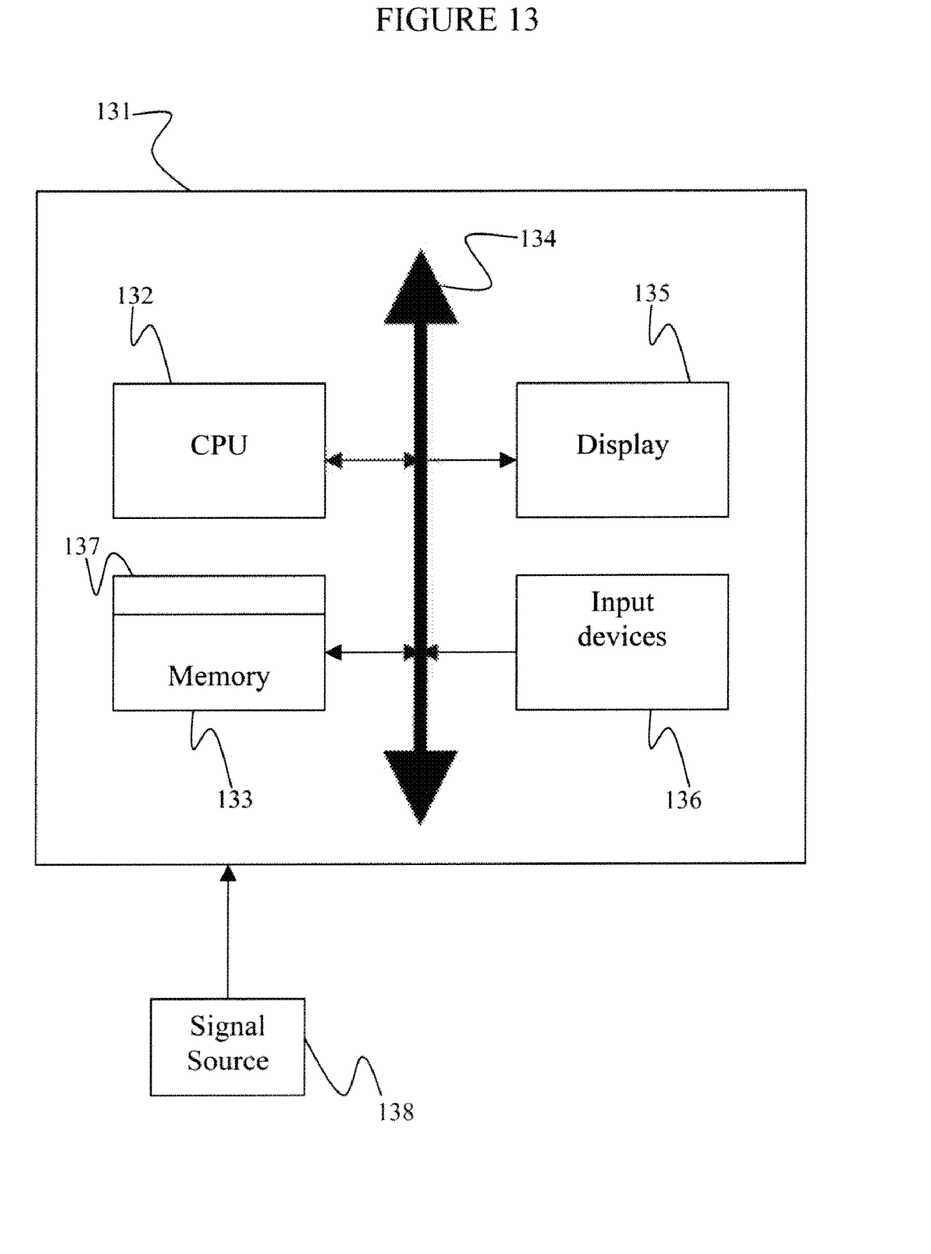
FIG. 13 is a block diagram of an exemplary computer system for implementing a method for automatically creating medical ontologies from semi-structured data, and to retrieving and combining information from multiple ontologies in the medical domain, according to an embodiment of the invention.

FIG. 13 is a block diagram of an exemplary computer system for implementing a method for automatically creating medical ontologies from semi-structured data, and to retrieving and combining information from multiple ontologies in the medical domain, according to an embodiment of the invention. Referring now to FIG. 13, a computer system 131 for implementing the present invention can comprise, inter alia, a central processing unit (CPU) 132, a memory 133 and an input/output (I/O) interface 134. The computer system 131 is generally coupled through the I/O interface 134 to a display 135 and various input devices 136 such as a mouse and a keyboard. The support circuits can include circuits such as cache, power supplies, clock circuits, and a communication bus. The memory 133 can include random access memory (RAM), read only memory (ROM), disk drive, tape drive, etc., or a combinations thereof. The present invention can be implemented as a routine 137 that is stored in memory 133 and executed by the CPU 132 to process the signal from the signal source 138. As such, the computer system 131 is a general purpose computer system that becomes a specific purpose computer system when executing the routine 137 of the present invention.

The computer system 131 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method for creating and searching medical ontologies comprising the steps of:

providing a semi-structured information source comprising a plurality of articles linked to each other, each article having one or more sections, wherein each article is associated with a concept;

creating a directed unlabeled graph representative of said information source, wherein each graph node is associated with a concept and each graph edge is associated with a link between concepts;

providing a plurality of labels, and labeling a subset of said edges of said graph;

assigning, by a processor, each unlabeled edge an equal probability of being assigned one of said plurality of labels;

updating, for each node, the probability of each outgoing edge by smoothing each said probability by an overall probability distribution of labels over all outgoing edges of each node;

updating, for each node, the probability of each incoming edge by smoothing each said probability by an overall probability distribution of labels over all incoming edges of each node; and assigning a label with a maximum probability to an edge if said maximum probability is greater than a predetermined threshold to create a labeled graph, wherein said labeled graph represents a new ontology configured to be searched.

2. The method of claim 1, further comprising repeating said steps of updating, for each node, the probability of each outgoing edge and updating, for each node, the probability of each incoming edge.

3. The method of claim 1, further comprising discarding an edge if said maximum probability for a label is less than said predetermined threshold.

4. The method of claim 1, wherein updating, for each node, the probability of each outgoing or incoming edge comprises calculating $$P_{ik} \leftarrow \frac{P_{ik} \times \sum_{j=1}^{n} P_{jk}}{\sum_{l=1}^{m} \left( P_{il} \times \sum_{j=1}^{n} P_{jl} \right)}$$

where $P_{ik}$ is the probability of edge i having label k, the sum in the numerator and the inner sum in the denominator are over all outgoing or incoming edges, and the outer sum in the denominator is over all labels.

5. The method of claim 1, wherein labeling a subset of said edges of said graph comprises finding a first article having a list a concepts, finding an instance of a concept in said list of concepts in a section of a second article, and assigning a title of said section of said second article as a label of an edge from said second article to said concept.

6. The method of claim 1, wherein labeling a subset of said edges of said graph comprises finding a concept in a list of concepts in a section of an article, and assigning a title of said section as a label of an edge from said article to said concept.

7. The method of claim 1, further comprising the step of extracting from said information source a plurality of concepts and a plurality of links, each link representative of a relationship between two or more of the plurality of concepts.

8. The method of claim 1, wherein each label of the plurality of labels represents a relationship between two concepts.

9. In a non-transitory computer readable program storage device having stored therein a program of instructions executable by the computer for creating and searching medical ontologies, the program storage device comprising instructions for:
providing a semi-structured information source comprising a plurality of articles linked to each other, each article having one or more sections, wherein each article is associated with a concept;
creating a directed unlabeled graph representative of said information source, wherein each graph node is associated with a concept and each graph edge is associated with a link between concepts;
providing a plurality of labels, and labeling a subset of said edges of said graph;
assigning each unlabeled edge an equal probability of being assigned one of said plurality of labels;
updating, for each node, the probability of each outgoing edge by smoothing each said probability by an overall probability distribution of labels over all outgoing edges of each node;
updating, for each node, the probability of each incoming edge by smoothing each said probability by an overall probability distribution of labels over all incoming edges of each node; and
assigning a label with a maximum probability to an edge if said maximum probability is greater than a predetermined threshold to create a labeled graph, wherein said labeled graph represents a new ontology configured to be searched.

10. The non-transitory computer readable program storage device of claim 9, the method further comprising repeating said steps of updating, for each node, the probability of each outgoing edge and updating, for each node, the probability of each incoming edge.

11. The non-transitory computer readable program storage device of claim 9, the method further comprising discarding an edge if said maximum probability for a label is less than said predetermined threshold.

12. The non-transitory computer readable program storage device of claim 9, wherein updating, for each node, the probability of each outgoing or incoming edge comprises calculating $$P_{ik} \leftarrow \frac{P_{ik} \times \sum_{j=1}^{n} P_{jk}}{\sum_{l=1}^{m} \left( P_{il} \times \sum_{j=1}^{n} P_{jl} \right)}$$

where $P_{ik}$ is the probability of edge i having label k, the sum in the numerator and the inner sum in the denominator are over all outgoing or incoming edges, and the outer sum in the denominator is over all labels.

13. The non-transitory computer readable program storage device of claim 9, wherein labeling a subset of said edges of said graph comprises finding a first article having a list a concepts, finding an instance of a concept in said list of concepts in a section of a second article, and assigning a title of said section of said second article as a label of an edge from said second article to said concept.

14. The non-transitory computer readable program storage device of claim 9, wherein labeling a subset of said edges of said graph comprises finding a concept in a list of concepts in a section of an article, and assigning a title of said section as a label of an edge from said article to said concept.

* * * * *